US00PP22369P2

(12) United States Plant Patent
Stemkens

(10) Patent No.: US PP22,369 P2
(45) Date of Patent: Dec. 20, 2011

(54) ***ACHILLEA* PLANT NAMED 'DESYEL'**

(50) Latin Name: *Achillea tormentosa×millifolium*
Varietal Denomination: Desyel

(75) Inventor: Henricus Godefriedus Wilhelmus Stemkens, Enkhuizen (NL)

(73) Assignee: Syngenta Crop Protection AG, Basel (CH)

( * ) Notice: Subject to any disclaimer, the term of this patent is extended or adjusted under 35 U.S.C. 154(b) by 0 days.

(21) Appl. No.: 12/924,178

(22) Filed: Sep. 22, 2010

(51) Int. Cl.
*A01H 5/00* (2006.01)

(52) U.S. Cl. ..... Plt./263.1

(58) Field of Classification Search ..... Plt./263.1
See application file for complete search history.

*Primary Examiner* — Annette Para

(74) *Attorney, Agent, or Firm* — S. Matthew Edwards

(57) ABSTRACT

A new *Achillea* plant named 'Desyel' particularly distinguished by the yellow flowers on strong upright inflorescences, compact and mounding habit with very fine fern-like medium-green foliage.

1 Drawing Sheet

Latin name of the genus and species of the plant claimed: *Achillea tormentosa×millifolium.*

Varietal denomination: 'Desyel'.

BACKGROUND OF THE NEW PLANT

The present invention comprises a new *Achillea*, botanically known as *Achillea tormentosa×millifoium*, and hereinafter referred to by the variety name 'Desyel'.

'Desyel' is a product of a planned breeding program. The new cultivar has yellow flowers on strong upright inflorescences, compact and mounding habit with very fine fern-like medium-green foliage.

'Desyel' originated from a hybridization made in summer 2002 in a controlled breeding environment in Enkhuizen, Netherlands.

The female parent was the unpatented, proprietary plant designated 'G6331-1', a *Achillea tomentosa* species with yellow flowers. 'G6331-1' has less vigor and a smaller plant habit than 'Desyel'.

The male parent of 'Desyel' was an unknown *Achillea milliforium* species plant. The resultant seed was sown in March 2003.

'Desyel' was selected as one flowering plant within the progeny of the stated cross in July 2003 in a controlled environment in Enkhuizen, Netherlands.

The first act of asexual reproduction of 'Desyel' was accomplished when vegetative cuttings were propagated from the initial selection in July 2003 in a controlled environment in Enkhuizen, Netherlands.

BRIEF SUMMARY OF INVENTION

Horticultural examination of plants grown from cuttings of the plant initiated in July 2003, and continuing thereafter, has demonstrated that the combination of characteristics as herein disclosed for 'Desyel' are firmly fixed and are retained through successive generations of asexual reproduction.

'Desyel' has not been observed under all possible environmental conditions. The phenotype may vary significantly with variations in environment such as temperature, light intensity and day length.

Plant Breeder's Rights for this cultivar were applied for in Canada on Oct. 6, 2009 (09-6733) and in CVPO on Sep. 23, 2010 (2009/1852). 'Desyel' has not been made publicly available more than one year prior to the filing of this application.

The following traits have been repeatedly observed and are determined to be basic characteristics of the new variety. The combination of these characteristics distinguishes this *Achillea* as a new and distinct variety.

BRIEF DESCRIPTION OF THE PHOTOGRAPH

The accompanying photographic drawing shows typical flower and foliage characteristics of 'Desred' with colors being as true as possible with an illustration of this type. The photographic drawing shows a flowering potted plant of the new variety, and a close-up of the flowers.

DETAILED BOTANICAL DESCRIPTION

The aforementioned photographs were taken in late August 2010 from plants growing in an outdoors trial in Gilroy, Calif. These plants were growing in gallon pots and were approximately 20 weeks of age.

The plant descriptions and measurements were taken in September 2010 in Gilroy, Calif. on 20-22 week old plants that were growing in 6-inch pots growing in a greenhouse.

Color Chart used: Royal Horticultural Society Colour Chart (R.H.S.) 2001

TABLE 1

DIFFERENCES BETWEEN THE NEW VARIETY 'DESYEL' AND A SIMILAR VARIETY

| | 'Desyel' | *Achillea* 'Taygetea' (Unpatented) |
|---|---|---|
| Flower color: | Lighter yellow | More yellow |
| Plant height: | Shorter | Taller |
| Leaf size: | Smaller | Bigger |
| Flowering response: | 3 weeks earlier | Later |

Plant:
*Form, growth and habit.*—Compact and mounding plant habit; strong inflorescences; freely flowering habit.
*Plant height.*—7-8 cm.
*Plant height (inflorescence included).*—20-24 cm.
*Plant width.*—30-35 cm.
Roots:
*Number of days to initiate roots.*—About 4-6 days at about 22 degrees C.
*Number of days to produce a rooted cutting.*—About 12-15 days at 22 degrees C.
*Type.*—Fine, fibrous, free branching.
*Color.*—RHS N155B but whiter.
Foliage:
*Arrangement.*—Alternate, simple.
*Immature, leaf color, upper surface.*—Between RHS 138A and RHS 138B.
*Lower surface.*—Closest to RHS 138B.
*Mature, leaf color, upper surface.*—Between RHS 138A and RHS 138B.
*Lower surface.*—Closest to RHS 138B.
*Length.*—10-13 cm.
*Width.*—2.0-2.4 cm.
*Shape.*—Ligulate.
*Base shape.*—Cuncate.
*Apex shape.*—Acute.
*Margin.*—Very finely dissected giving a fern-like appearance.
*Texture, upper surface.*—Pilose.
*Lower surface.*—Pilose.
*Color of veins, upper surface.*—RHS 138D.
*Color of veins, lower surface.*—RHS 138D.
Stem:
*Color of stem.*—RHS 138B to RHS 138C but a little more yellow-green.
*Length of stem.*—About 25 cm.
*Diameter.*—0.4 cm.
*Length of internodes.*—2.0-3.0 cm.
*Texture.*—Pilose.
*Color of peduncle.*—RHS 138B to RHS 138C but a little more yellow-green.
*Length of peduncle.*—2.5-3.0 cm.
*Peduncle diameter.*—0.2 cm.
*Texture.*—Pilose or dendritic hairs.
*Color of pedicel.*—RHS 138C.
*Length of pedicel.*—0.4-0.5 cm.
*Pedicel diameter.*—0.075 cm.
*Texture.*—Pilose or dendritic hairs.
Inflorescence:
*Type.*—Rotate composite inflorescence form; inflorescences arranged in terminal or axillary compound cymes.
*Blooming habit.*—Free-flowering throughout the summer.
*Quantity of inflorescences per plant.*—Approximately 200.
*Lastingness of individual blooms on the plant.*—About 7 days.
*Fragrance.*—Faint.
Cyme:
*Diameter.*—6-7 cm.
*Height.*—4 cm.
Bud (just when opening/showing color):
*Color.*—RHS 7C.
*Length.*—0.6-0.7 cm.
*Width.*—0.2 cm.
*Shape.*—Ovoid.
Immature inflorescence:
*Diameter.*—0.5 cm.
*Color of ray florets, upper surface.*—RHS 3A.
*Lower surface.*—RHS 4A.
Mature inflorescence:
*Diameter.*—0.8-0.9 cm.
*Depth/height.*—0.7 cm.
*Total diameter of 'disc'.*—0.3-0.35 cm.
*Receptacle height.*—0.4-0.5 cm.
*Receptacle diameter.*—0.35 cm.
Ray florets:
*Average quantity of florets.*—4-5 in 1 whorl.
*Color of florets, upper surface.*—RHS 3A.
*Lower surface.*—RHS 4A.
*Length.*—0.3 cm.
*Width.*—0.3 cm.
*Shape.*—Obovate.
*Apex shape.*—Irregularly emarginate.
*Margin.*—Entire.
*Texture, upper surface.*—Papillose.
*Lower surface.*—Papillose.
Disc florets:
*Average quantity of florets.*—About 20-25.
*Color of florets.*—RHS 13B with RHS 138B basally.
*Length.*—0.5 cm.
*Width.*—0.1 cm.
*Shape.*—Tubular.
*Apex shape.*—5-pointed.
Phyllaries:
*Quantity.*—About 20.
*Color, upper surface.*—RHS 145C.
*Lower surface.*—RHS 145B.
*Length.*—0.2-0.4 cm.
*Width.*—0.1 cm.
*Shape.*—Lanceolate.
*Apex shape.*—Acute.
*Based.*—Fused.
*Margins.*—Entire with papery edges.
*Texture, upper surface.*—Glabrous.
*Lower surface.*—Pilose or dendritic hairs.
Reproduction organs:
*Gynoecium.*—Found on both floret types.
*Pistil.*—1.
*Length.*—0.4-0.5 cm.
*Style color.*—RHS 155C.
*Style length.*—0.3-0.4 cm.
*Stigma color.*—RHS 13C.
*Stigma shape.*—Bi-parted.
*Ovary color.*—Not observed.
*Androcium.*—Found only on disc florets.
*Stamens.*—5.
*Color of filaments.*—RHS 155C.
*Length of filaments.*—0.3 cm.
*Anther color.*—RHS 12C.
*Anther length.*—0.1 cm.
*Anther shape.*—Ovate to rounded.
*Color of pollen.*—RHS 14B.
*Pollen amount.*—Good.
*Fertility/seed set.*—Has not been observed on this hybrid.
Disease/pest resistance: Disease/pest resistance has not been observed on this hybrid.

What is claimed is:

1. A new and distinct variety of *Achillea* plant named 'Desyel' substantially as illustrated and described herein.

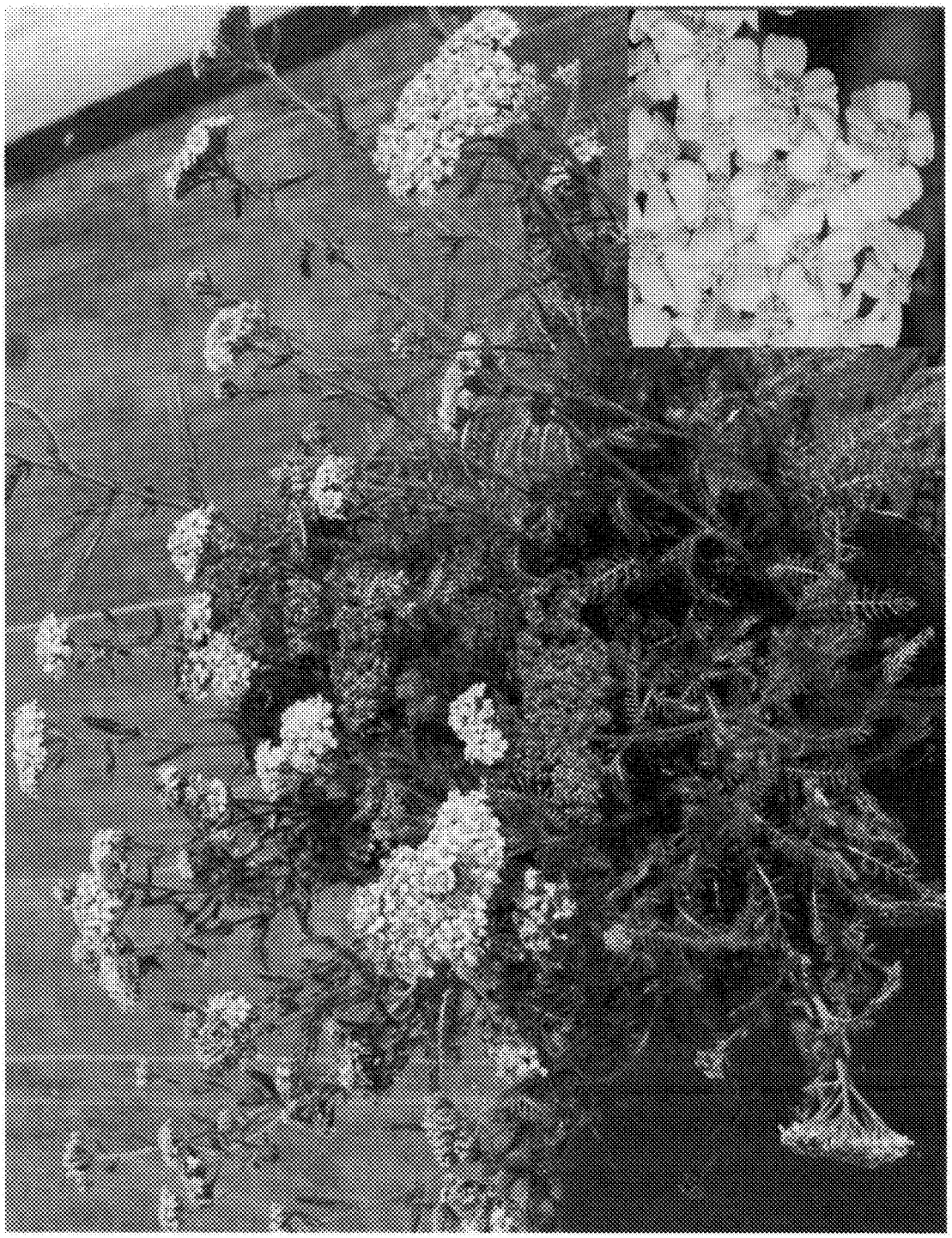

* * * * *